US009677981B2

(12) United States Patent
Sitton et al.

(10) Patent No.: US 9,677,981 B2
(45) Date of Patent: Jun. 13, 2017

(54) SAMPLE CONCENTRATOR AND METHOD OF USE

(71) Applicant: 3M INNOVATIVE PROPERTIES COMPANY, St. Paul, MN (US)

(72) Inventors: Gregory W. Sitton, Minneapolis, MN (US); Andrew H. Tilstra, Shoreview, MN (US); Wensheng Xia, Woodbury, MN (US); Jon A. Kirschhoffer, Stillwater, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 0 days.

(21) Appl. No.: 14/774,149

(22) PCT Filed: Mar. 13, 2014

(86) PCT No.: PCT/US2014/025166
§ 371 (c)(1),
(2) Date: Sep. 10, 2015

(87) PCT Pub. No.: WO2014/151177
PCT Pub. Date: Sep. 25, 2014

(65) Prior Publication Data
US 2016/0025607 A1 Jan. 28, 2016

Related U.S. Application Data

(60) Provisional application No. 61/786,957, filed on Mar. 15, 2013.

(51) Int. Cl.
*G01N 1/40* (2006.01)
*C12Q 1/04* (2006.01)
*B01L 3/00* (2006.01)
*C12Q 1/24* (2006.01)
*G01N 33/569* (2006.01)
*C12Q 1/68* (2006.01)
*G01N 15/06* (2006.01)

(52) U.S. Cl.
CPC ............ *G01N 1/4077* (2013.01); *B01L 3/508* (2013.01); *B01L 3/50255* (2013.01); *C12Q 1/04* (2013.01); *C12Q 1/24* (2013.01); *G01N 1/40* (2013.01); *G01N 33/56911* (2013.01); *B01L 2200/0647* (2013.01); *B01L 2200/0689* (2013.01); *B01L 2300/045* (2013.01); *B01L 2300/0681* (2013.01); *B01L 2300/0832* (2013.01); *B01L 2400/0475* (2013.01); *B01L 2400/0478* (2013.01); *C12Q 1/6844* (2013.01); *G01N 15/0618* (2013.01); *G01N 2001/4088* (2013.01); *G01N 2333/00* (2013.01); *G01N 2333/195* (2013.01)

(58) Field of Classification Search
CPC ........ G01N 1/40; G01N 1/4077; G01N 33/50; G01N 33/569; G01N 33/56911; C12Q 1/04; C12Q 1/24; B01L 3/508; B01L 3/50; B01L 3/502; B01L 3/50255; B01L 2300/046; B01L 2300/06; B01L 2300/0681
See application file for complete search history.

(56) References Cited

U.S. PATENT DOCUMENTS

| | | | |
|---|---|---|---|
| 5,989,431 A | 11/1999 | Evans et al. | |
| 6,277,648 B1 | 8/2001 | Colpan | |
| 7,371,545 B2 | 5/2008 | Tisi et al. | |
| 7,374,913 B2 | 5/2008 | Nagamine | |
| 7,494,790 B2 | 2/2009 | Notomi et al. | |
| 7,727,710 B2 | 6/2010 | Haddad et al. | |
| 8,309,308 B2 | 11/2012 | Tisi et al. | |
| 8,322,539 B1 | 12/2012 | Ellis et al. | |
| 2002/0010323 A1 | 1/2002 | Mitchell et al. | |
| 2005/0064585 A1 | 3/2005 | Wolf et al. | |
| 2005/0115903 A1 | 6/2005 | Hallier-Soulier et al. | |
| 2005/0191619 A1 | 9/2005 | Davis et al. | |
| 2008/0113357 A1 | 5/2008 | Baggio et al. | |
| 2008/0118921 A1 | 5/2008 | Tisi et al. | |
| 2008/0299621 A1 | 12/2008 | Tatnell et al. | |
| 2009/0226910 A1 | 9/2009 | Isac et al. | |
| 2009/0238725 A1 | 9/2009 | Ellis et al. | |
| 2012/0027699 A1 | 2/2012 | Rosa et al. | |
| 2012/0157326 A1 | 6/2012 | Tisi et al. | |

(Continued)

FOREIGN PATENT DOCUMENTS

| | | |
|---|---|---|
| EP | 1 588 764 | 10/2005 |
| GB | 786824 | 11/1957 |
| JP | 2-255074 | 10/1990 |

(Continued)

OTHER PUBLICATIONS

Gandelman, O.A. et al.; "Novel Bioluminescent Quantitative Detection of Nucleic Acid Amplification in Real-Time"; PLoS ONE; vol. 5, No. 11; 2010; pp. e14155 (13 pgs).

*Primary Examiner* — Jennifer McDonald
*Assistant Examiner* — Qing Xu
(74) *Attorney, Agent, or Firm* — 3M Innovative Properties Company; Eric E. Silverman

(57) ABSTRACT

The present disclosure provides an assembly for preparing a sample for analysis. The assembly comprises a hollow body comprising first opening, an outlet with a second opening, and a fluid pathway extending therebetween; a filter element operatively interposed in the fluid pathway; and a closure comprising a third opening and a chamber, the closure being slideably engaged with the outlet. The chamber and the outlet are dimensioned so that the outlet is sealingly engaged with the chamber. A method of using the assembly to detect a microorganism is also provided.

10 Claims, 7 Drawing Sheets

(56) References Cited

U.S. PATENT DOCUMENTS

2014/0014579 A1    1/2014    Haruna

FOREIGN PATENT DOCUMENTS

| WO | WO 98/56484    | 12/1998 |
| WO | WO 2004/009840 | 1/2004  |
| WO | WO 2005/090567 | 9/2005  |
| WO | WO 2009/046191 | 4/2009  |
| WO | WO 2010/078404 | 7/2010  |
| WO | WO 2011/068465 | 6/2011  |
| WO | WO 2012/122088 | 9/2012  |

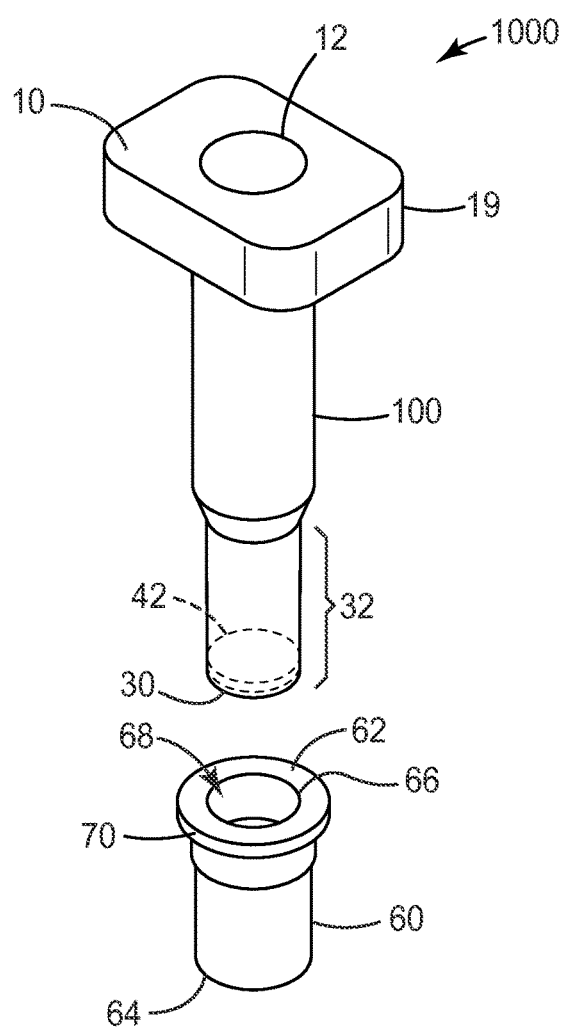
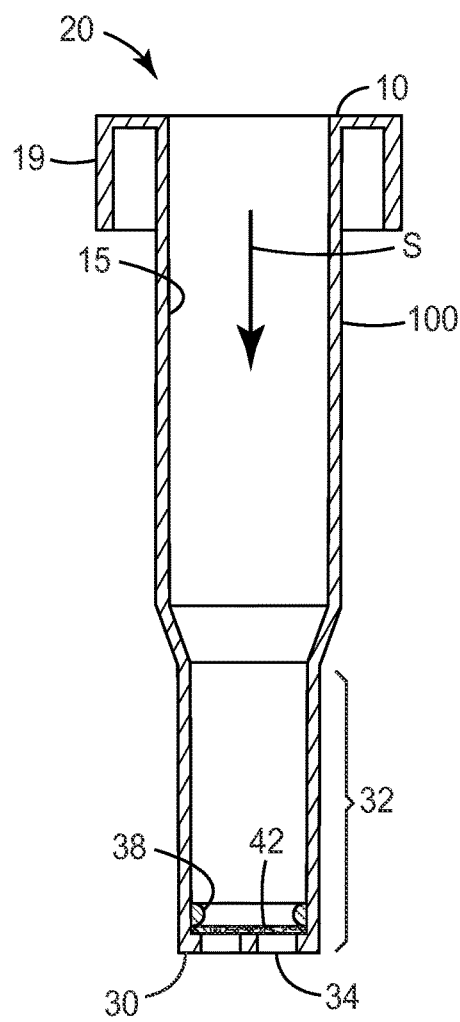
FIG. 1
FIG. 2
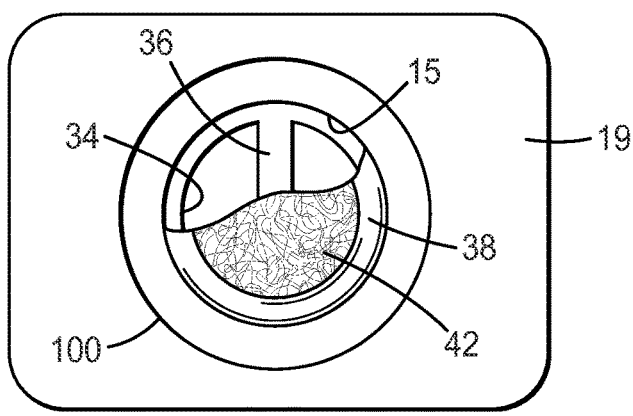
FIG. 3

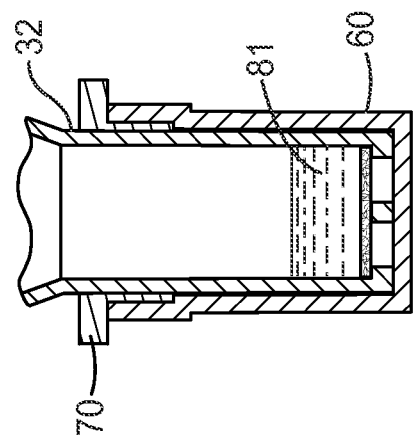
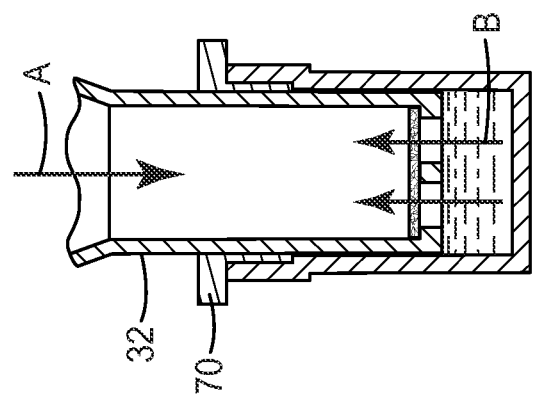
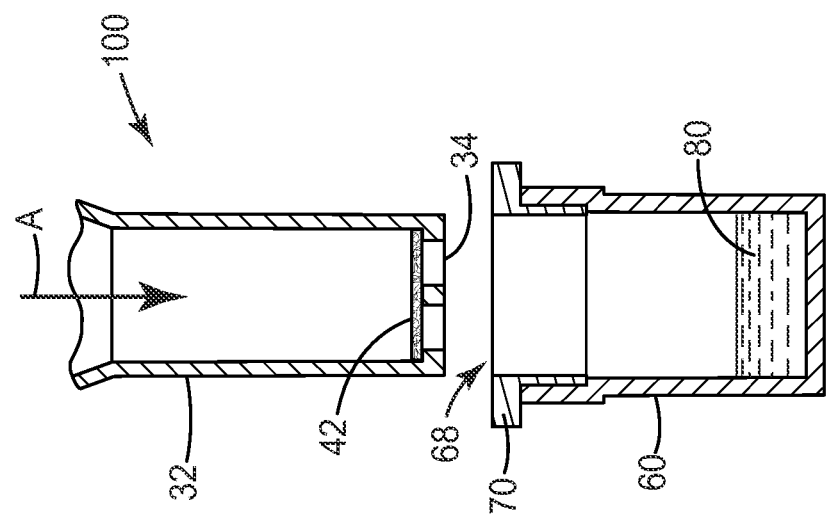

SAMPLE CONCENTRATOR AND METHOD OF USE

CROSS REFERENCE TO RELATED APPLICATIONS

This application is a national stage filing under 35 U.S.C. 371 of PCT/US2014/025166, filed Mar. 13, 2014, which claims priority to U.S. Provisional Patent Application No. 61/786,957, filed Mar. 15, 2013, the disclosure of which is incorporated by reference in its entirety herein.

BACKGROUND

Many types of samples (e.g., clinical, environmental, food, and beverage samples) are routinely tested for the presence or absence of microorganisms. In particular many samples are tested for the presence of pathogenic microorganisms. Often, the samples require various types of pretreatment (i.e., processing prior to a detection step) in order to increase the number of target microorganisms, decrease the number of non-target microorganisms, concentrate the microorganisms, and/or reduce the quantity of potentially-interfering material in the sample. The pre-treatment steps may be laborious and can take several hours to several days to complete. A variety of materials and devices have been developed to reduce the number of steps and the time that it takes to complete the pre-treatment of samples.

Processing a plurality of samples simultaneously can be difficult because of the lack of simple, efficient devices for the procedure. There remains a need for simple, rapid methods to prepare one or more samples for the detection of microorganisms.

SUMMARY

The present disclosure generally relates to the detection of a microorganism in a sample. In particular, the present disclosure relates to an assembly and method for detecting a presence or absence of a microorganism in a liquid sample. The inventive assembly can be used in a simple, rapid method to detect very low numbers of microorganisms in a sample.

In one aspect, the present disclosure provides an assembly. The assembly can comprise a hollow body comprising a first opening, an outlet with a second opening, and a fluid pathway extending therebetween; a filter element operatively interposed in the fluid pathway; and a closure comprising a third opening and a chamber, the closure being slideably engaged with the outlet. The chamber and the outlet are dimensioned so that the outlet is sealingly engaged with the chamber. In any embodiment, the hollow body further can comprise a reservoir dimensioned to receive a predefined volume of liquid sample, wherein the fluid pathway comprises the reservoir.

In another aspect, the present disclosure provides an assembly. The assembly can comprise a first body comprising a plurality of hollow channels, each hollow channel extending from a first opening to a second opening, each second opening being disposed in one of a plurality of outlets; a plurality of filter elements, wherein each of the filter elements is operatively interposed in one of the plurality of hollow channels; and a plurality of closures, each closure comprising a third opening and a chamber, each of the plurality of closures being slideably engaged with a different outlet of the plurality of outlets; Each of the plurality of closures and each of the plurality of outlets are dimensioned so that one of the plurality of outlets is sealingly engaged with a corresponding chamber of the plurality of chambers. In any embodiment, the body further can comprise a plurality of reservoirs, each reservoir being dimensioned to receive a predefined volume of liquid sample.

In any of the above embodiments, the body further can comprise a first engagement structure, wherein the closure further can comprise a second engagement structure complementary to the first engagement structure. In any of the above embodiments, the assembly further can comprise a reagent disposed in at least one of the pathways or at least one of the closures.

In any of the above embodiments, the assembly can comprise a first fluid pathway extending to a first second opening at a first outlet, a first filter element operatively interposed in the first fluid pathway, and a first closure having a chamber dimensioned to sealingly receive the first outlet. The first fluid pathway can comprise two volumes defined by the filter element: a first volume extending from the filter element to the first opening and a second volume extending from the disposed between the filter element and the second opening. The chamber of the first closure defines a third volume that is greater than the second volume.

In yet another aspect, the present disclosure provides a method. The method can comprise depositing a liquid sample suspected of containing a microorganism into a sample preparation device, the sample preparation device comprising: a hollow body comprising first opening, an outlet with a second opening, and a fluid pathway extending therebetween; and a filter element operatively interposed in the fluid pathway. The method further can comprise urging the outlet into a chamber configured to sealingly receive the outlet, the chamber containing a back-flush liquid; and analyzing a portion of the back-flush liquid to detect a presence or an absence of the microorganism. Urging the outlet into the chamber comprises urging the outlet into the chamber to an extent sufficient to cause the back-flush liquid to contact the filter element.

In any embodiment of the method, urging the outlet into the chamber can comprise urging the outlet into the chamber to an extent sufficient to cause a portion of the back-flush liquid to pass through the filter element. In any embodiment, analyzing a portion of the back-flush liquid to detect a presence or an absence of the microorganism can comprise analyzing a quantity of the portion of the back-flush liquid.

In yet another aspect, the present disclosure provides a kit. The kit can comprise a hollow body comprising first opening, an outlet with a second opening, and a fluid pathway extending therebetween; a filter element operatively interposed in the fluid pathway; and a closure comprising a third opening and a chamber, wherein the chamber and the outlet are configured so that the second end can be sealingly received in the chamber.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. Thus, for example, an article comprising "a" filter element can be interpreted to mean that the article can comprise "one or more" filter elements.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

The features and advantages of the present invention will be understood upon consideration of the detailed description of the preferred embodiment as well as the appended claims. These and other features and advantages of the invention may be described below in connection with various illustrative embodiments of the invention.

The above summary of the present invention is not intended to describe each disclosed embodiment or every implementation of the present invention. The Figures and the detailed description which follow more particularly exemplify illustrative embodiments. Other features, objects and advantages will become apparent from the description and drawings, and from the claims.

BRIEF DESCRIPTION OF DRAWINGS

FIG. 1 is a partially-exploded perspective view of one embodiment of an assembly comprising a body and a closure according to the present disclosure.

FIG. 2 is a cross-sectional side view of the body of FIG. 1.

FIG. 3 is a top view, partially in section, of the body of FIG. 2.

FIGS. 6A-6C are cross-sectional side views of an outlet portion of a body and a closure during sequential steps in a process of operationally coupling the body with the closure.

DETAILED DESCRIPTION

Figure 4:
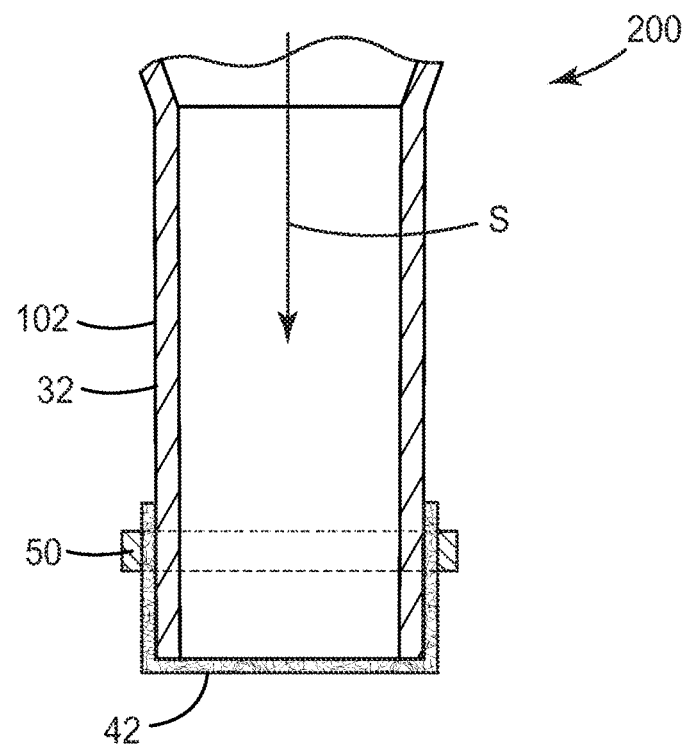
FIG. 4 is a cross-sectional side view of the outlet portion of an alternative embodiment of a body comprising an outlet having an external filter element operatively disposed in a fluid pathway according to the present disclosure.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "connected" and "coupled" and variations thereof are used broadly and encompass both direct and indirect connections and couplings. Further, "connected" and "coupled" are not restricted to physical or mechanical connections or couplings. It is to be understood that other embodiments may be utilized and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to preparing a sample for detecting the presence or absence of an analyte. In particular, the present disclosure provides an assembly and a method to capture one or more microorganisms using a filter and efficiently permeabilize the microorganism to make the microorganism's nucleic acid suitable for amplification. Advantageously, the capture of microorganisms from a sample and the subsequent permeabilization may be accomplished in the assembly using just two steps—filter and back-flush. The resulting captured microorganisms are relatively concentrated, relatively free of impurities, and are suitable for use in a variety of detection methods (e.g., immunodetection methods and, in particular, nucleic acid detection methods such as the LAMP-Bart detection method described by Gandelman et al. (Gandelman O A, Church V L, Moore C A, Kiddle G, Carne C A, et al. (2010) Novel Bioluminescent Quantitative Detection of Nucleic Acid Amplification in Real-Time. PLoS ONE 5(11): e14155).

In addition to an assembly and method for processing a single sample, the present disclosure also includes methods and an assembly for processing (e.g., simultaneously or sequentially) a plurality of samples. The inventive methods relate to the detection of an analyte in a sample. In any embodiment, the analyte can be a biological analyte such as, for example, a DNA molecule that comprises a polynucleotide sequence that indicates the presence of a particular microorganism (e.g., a particular pathogenic microorganism) in the sample.

The plurality of samples may comprise samples from independent sources. Alternatively or additionally, the samples may comprise samples obtained from a single source (e.g., replicate sample; samples removed at different time points; replicate samples that were subjected to different treatments). The inventive methods relate to the detection of an analyte in a sample. In any embodiment, the analyte can be a biological analyte such as, for example, a biological analyte that indicates the presence of a microorganism in the sample.

The sample can be any filterable sample that may comprise a microorganism. Nonlimiting examples of suitable samples include suspensions or cultures of cells, environmental samples (e.g., material picked up using surface swabs) suspended in a liquid suspending medium, food (e.g., liquid food materials and/or solid food materials suspended in a liquid medium), beverages, clinical samples (e.g., blood, urine, sputum, tissue, mucous, feces, wound exudate, pus; optionally suspended in a liquid suspending medium), and water (e.g., surface water, potable water, process water).

Besides fluid samples, other test samples may include liquids as well as solid(s) dissolved or suspended in a liquid medium. Samples of interest may include process streams, water, soil, plants or other vegetation, air, surfaces (e.g., contaminated surfaces), and the like. Samples can also include cultured cells. Samples can also include samples obtained from a device comprising cells and/or spores (e.g., a biological indicator device).

Solid samples may be disintegrated (e.g., by blending, sonication, homogenization) in a liquid suspending medium (e.g., water, buffer, broth). In any embodiment, the sample material may be eluted (e.g., rinsed, scraped, expressed) from a sample-collection device (e.g., a swab, a sponge, a wipe, a scraper) and suspended in a suspending medium, if necessary to filter it, before using the sample material in the method. In some embodiments, liquid or solid samples may be diluted in a liquid (e.g., water, buffer, broth).

Microorganisms analyzed in a test sample may be derived from a variety of sources, as described herein. Microorganisms of particular interest include prokaryotic and eukaryotic organisms, particularly Gram positive bacteria, Gram negative bacteria, fungi, protozoa, *mycoplasma*, and yeast. Particularly relevant organisms include members of the family Enterobacteriaceae, or the family Micrococcaceae or the genera *Staphylococcus* spp., *Streptococcus* spp., *Pseudomonas* spp., *Enterococcus* spp., *Salmonella* spp., *Legionella* spp., *Shigella* spp. *Yersinia* spp., *Enterobacter* spp., *Escherichia* spp., *Bacillus* spp., *Listeria* spp., *Vibrio* spp., *Corynebacteria* spp., *Aspergillus* spp., *Fusarium* spp., and *Candida* spp. Particularly virulent organisms include *Staphylococcus aureus* (including resistant strains such as Methicillin Resistant *Staphylococcus aureus* (MRSA)), *S. epidermidis, Streptococcus pneumoniae, S. agalactiae, S. pyogenes, Enterococcus faecalis*, Vancomycin Resistant *Enterococcus* (VRE), Vancomycin Resistant *Staphylococcus aureus* (VRSA), Vancomycin Intermediate-resistant *Staphylococcus aureus* (VISA), *Bacillus anthracia, Pseudomonas aeruginosa, Escherichia coli, Aspergillus niger, A. fumigatus, A. clavatus, Fusarium solani, F. oxysporum, F. chlamydosporum, Listeria monocytogenes, Listeria ivanovii, Campylobacter* species, *Vibrio cholera, V. parahemolyticus, Salmonella cholerasuis, S. typhi, S. typhimurium, Candida albicans, C. glabrata, C. krusei, Enterobacter sakazakii, E. coli* O157 and multiple drug resistant Gram negative rods (MDR).

In order to facilitate a complete understanding, the remainder of the detailed description describes apparatuses and assemblies for processing a sample by reference to the drawings, wherein like elements among the embodiments are referenced with like numerals throughout the following description. Turning to the drawings, FIG. 1 is a partially-exploded perspective view of one embodiment of an assembly 1000 according to the present disclosure. The assembly 1000 comprises a hollow body 100 with a closure 60 sealingly coupled thereto. FIG. 2 is a cross-sectional view of the body 100 of the assembly 1000 of FIG. 1.

In the illustrated embodiment, the body 100 comprises a first end 10 and a second end 30 opposite the first end. The first end 10 comprises a first opening 12, which provides fluidic access to a reservoir 20 in the body 100. The second end 30 comprises an outlet 32 having a second opening 34 that provides fluidic egress from the body 100. Thus, the body 100 comprises a fluid pathway "S" extending from the first opening 12 through the reservoir 20 to the second opening 34. The body 100 can be made from any suitable material that is substantially impermeable to water using processes that are known in the art. Non-limiting examples of suitable materials include, for example, glass, plastic (e.g., polyethylene, polypropylene, polycarbonate), or metal. In any embodiment, the body 100 optionally may comprise a collar 19. The collar 19 can facilitate coupling the body 100 to a source of negative pressure to assist filtration of the sample, as described in U.S. Patent Application Publication No. US 2012/027699, which is incorporated herein by reference in its entirety.

The reservoir 20 has at least one wall 15 and is configured (e.g., shaped, dimensioned) to hold a liquid (e.g., a liquid sample to be tested for the presence or absence of an analyte such as a microorganism or a component thereof, for example). The reservoir can be dimensioned to receive a predefined volume such as, for example, about 0.1 milliliter, about 0.5 milliliter, about 1 milliliter, about 5 milliliters, about 10 milliliters, about 20 milliliters, about 25 milliliters, about 50 milliliters, about 100 milliliters, or greater than 100 milliliters of liquid. The liquid (not shown) can be deposited into the reservoir 20 via the first opening 12.

In any embodiment a portion of the interior surface or the entire interior surface of the body 100 (e.g., the interior surface that defines the fluid pathway "5") can comprise a coating of material that substantially prevents nonspecific adherence of biomolecules such as nucleic acids and proteins, for example, to the surface. A non-limiting example of a suitable coating material is a 0.3% by weight aqueous solution of Novec™ FC4430 Fluorosurfactant (3M Company). The FC4430 fluorosurfactant is described in U.S. Pat. No. 7,727,710, which is incorporated herein by reference in its entirety.

Operatively interposed in the fluid pathway S is a filter element 42. "Operatively interposed", as used herein, means that a fluid moving through the fluid pathway from one end (e.g., from the first opening 12 of the first end 10 of the body 100) to the other end (e.g., out of the second opening 34 of the second end 30 of the body 100) passes through the filter element (e.g., filter element 42). Proximate the second opening 34 is a support piece 36, on which the filter element 42 is disposed. Optionally, the filter element 42 may be coupled to a portion of the body 100 (e.g., the wall 15 or the support piece 36) using means that are known in the art (e.g., an adhesive, a heat weld). Alternatively or additionally, in any embodiment, the filter element may be secured in a fixed position against the support piece using, for example, an O-ring 38. The O-ring 38 may be secured to the body 100 by an adhesive, a heat weld, or by friction-fit, for example. FIG. 3 shows a top view, partially in section, of the body 100; showing the O-ring 38, the filter element 42, the support piece 36, and the second opening 34.

As an alternative to positioning the filter element in an interior region (e.g., in the reservoir 20) of the body, as shown in FIG. 2, it is contemplated that the filter element may be disposed in the fluid pathway at a location exterior to the body. FIG. 4 shows a cross-sectional side view of one embodiment of a body 200 comprising a filter element 42 that is positioned exterior to the body 200. In the illustrated embodiment, the filter element 42 is used to cover the second opening 34 of the body 200. A portion of the filter element 42 extends up the exterior surface 102 of the outlet 32 and is secured in place by a gasket 50. The gasket 50 is made from a material and is dimensioned so that can be sealingly received in a closure (not shown in FIG. 4) according to the present disclosure. Preferred materials that may be used for the gasket 50 include conformable materials such as, for example, silicone or rubber, which can be slideably received into the closure 60 and form a seal that is substantially resistant to leakage of aqueous liquids. However, conformable materials are not required; in particular, in embodiments that include a sealing member described hereinbelow. It is contemplated the filter element 42 may be secured to the exterior surface 102 of the outlet by other means such as, for example, an adhesive or an ultrasonic weld, provided the secural means permits the outlet 32 to be sealingly received in the closure 60, as described herein.

The filter element 42 comprises any suitable filter medium capable of preventing the passage of a target microorganism therethrough. This includes, for example, membrane filters. Membrane filters are particularly preferred because of their relative ease of handling and the relatively low volume of liquid retained by a membrane filter after passing a liquid sample therethrough. In any embodiment, the filter element 42 can be selected to have a nominal porosity that should retain a target microorganism. For example, when the target microorganism is a bacterium or a bacterial spore, the nominal porosity of the filter element can be selected to retain bacteria or bacterial spores (e.g., a nominal porosity of about 0.45 µm, 0.22 µm, 0.2 µm, or 0.1 µm). When the target microorganism is a yeast or a mold microorganism, the nominal porosity of the filter element can be selected to retain the yeast or mold microorganisms (e.g., a nominal porosity of about 5.0 µm, 5.0 µm, 1.0 µm, or 0.45 µm). In any embodiment, the target microorganism may be captured (e.g., using a tethered antibody) on a particulate material that is larger than the target microorganism. In these embodiments, the nominal porosity of the filter element can be selected to retain the particles that are used to capture the microorganisms. A person having ordinary skill in the art will recognize filter materials with a porosity that is suitable for the particular microorganism to be detected.

Figure 5:
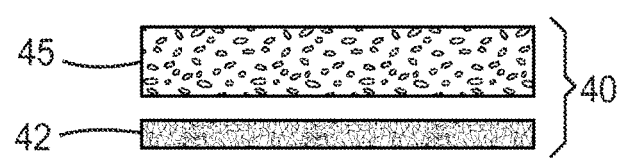
FIG. 5 is a side view of one embodiment of a filter stack according to the present disclosure.

In any embodiment, the assembly may comprise an optional prefilter 45 operatively disposed in the fluid pathway. In any embodiment, the prefilter 45 may be disposed adjacent the filter element 42 in a filter stack 40, as shown in FIG. 5. The filter stack 40 is operatively interposed in the fluid pathway in a manner similar to those described for the filter element 42. A prefilter 45 in a filter stack 40 is disposed in the fluid pathway proximate the first opening (not shown) and the filter element 42 in a filter stack 40 is disposed in the fluid pathway proximate the second opening (not shown). The components of the filter stack 40 (e.g., filter element 42 and prefilter 45) may be secured to the body 100 according to any of the secural means described for securing the filter element 42 to the body. In any embodiment, the filter stack may comprise a plurality of filter elements and, optionally, one or more prefilters (not shown).

Optionally, in any embodiment, the filter stack 40 may comprise a scrim (not shown) positioned on the upstream-side (e.g., proximate the first opening) of the prefilter 45, on the downstream-side (e.g., proximate the second opening) of the filter element 42, and/or positioned between the prefilter 45 and the filter element 42. Positioning the prefilter 45 adjacent the filter element 42 permits the operator to back-flush both of them simultaneously, as discussed below. This may enhance the sensitivity of the detection method as described herein.

Returning to FIG. 1, the assembly 1000 comprises a closure 60. The closure 60 has a first end 62 and a second end 64 opposite the first end 62. The first end 62 comprises a third opening 66. The third opening 66 provides access to a chamber 68. The closure 60 configured so that at least a portion of the outlet 32 can be received through the third opening 66 and into the chamber 68. Preferably, the portion of the outlet 32 is sealingly received into the closure 60. The closure 60 can be made from any suitable material that is substantially impermeable to water using processes that are known in the art. Non-limiting examples of suitable materials include, for example, glass, plastic (e.g., polyethylene, polypropylene, polycarbonate), or metal. During use, the closure 60 is coupled (e.g., sealingly coupled) to the outlet 32 of the body 100.

In any embodiment, the assembly may comprise a sealing member 70. The sealing member 70 can be coupled to the closure 60 (e.g., by friction fit) as shown in FIG. 1 or, similarly, to the outlet (not shown). The sealing member 70 can be made from conformable materials such as, for example, silicone or rubber, which can form a seal that is substantially resistant to leakage of aqueous liquids. In any embodiment, the sealing member 70 can be a septum (e.g., a deformable split septum) that is penetrable by the outlet 32. Thus, as the outlet 32 penetrates the septum, the septum forms a liquid-resistant seal around the outlet 32.

During use of the assembly, the chamber 68 of the closure 60 contains a back-flush liquid (not shown in FIG. 1) that is used to back-flush the filter element 42. Thus, when the outlet is urged into the chamber containing the back-flush liquid, the back-flush liquid is forced into the outlet of the body until the liquid contacts the filter element, as shown in FIGS. 6A-6C.

A back-flush liquid according to the present disclosure can be any suitable liquid that can permeate and, preferably, pass through the filter element 42 when introduced into the body 100 from the second opening 34 of the body. In any embodiment, when the back-flush liquid passes through the filter element 42 from the side proximate the second end 30 to the side proximate the first end 10, the back-flush liquid can cause a microorganism (e.g., a microorganism from a liquid sample that is passed through the body 100) on and/or in the filter element 42 to disengage from the filter element. In any embodiment, the back-flush liquid can comprise a reagent capable of permeabilizing a microorganism or a mammalian cell (e.g., EDTA, an alcohol (e.g., 70% ethanol), a biguanide (e.g., chlorhexidine gluconate), and/or formalin). In any embodiment, the back-flush liquid can comprise a reagent capable of lysing a microorganism (e.g., lysozyme, lysostaphin, TRITON X-100, proteinase K, mutanolysin). In any embodiment, the back-flush liquid may comprise a buffer reagent to buffer the liquid at a pH that is within a predefined pH range (e.g., from a pH about 6.5 to a pH about 8.5, from a pH about 7.0 to a pH about 8.0). Non-limiting examples of suitable back-flush liquids include water, phosphate buffer, Tris buffer, Denhardt's buffer, and normal saline.

In use, the outlet 32 of the body 100 is configured to be inserted into the chamber 68 of the closure 60 to facilitate back-flushing the filter element 42. FIG. 6A shows a portion (i.e., the outlet 32) of a body aligned to be inserted into a corresponding closure 60. The closure 60 includes a back-flush liquid 80 disposed in the chamber 68. In any embodiment, the outlet 32 can be urged by applying force to the body in the direction of arrow "A" and/or by applying force to the closure 60 (not shown) in a direction opposite arrow "A". As the outlet 32 moves further into the chamber 68, the second opening 34 contacts the surface of the back-flush liquid 80. Further movement of the outlet 32 into the chamber 68 causes the back-flush liquid 80 to move into the outlet 32 in the general direction of arrow "B" (shown in FIG. 6B) until the liquid 80 ultimately passes through filter element 42 and into the reservoir 20, as shown in FIG. 6C. At least a portion of the back-flush liquid 81 that has passed through the filter element 42 can be collected, for example, by inserting a pipette into the reservoir via the first opening of the body (not shown in FIG. 6C). The portion of back-flush liquid 81 collected from the body can be analyzed to detect a presence or an absence of a microorganism as described herein. Also shown in FIGS. 6A-6C is optional sealing element 70.

In any embodiment, the body and/or closure of the assembly of the present disclosure can comprise engagement structures configured to couple (e.g., releasably couple) the body and closure to each other. In addition, the engagement structures can also function to hold (e.g., releasably hold) the body and the closure in a predefined, fixed position, relative to each other. In any embodiment, the engagement structures may comprise a male terminal structure (e.g., a pin, peg, pin, plug, protrusion, or the like) disposed on or in one of the elements (e.g., the body) of the assembly and a corresponding female terminal structure (e.g., a socket, cavity, hole, receptacle, or the like) disposed on or in the other element (e.g., the closure) of the assembly.

Figure 7B:
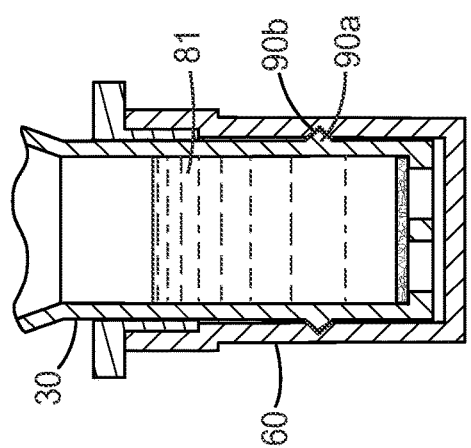
FIG. 7B is a cross-sectional side view of an assembly comprising the body and closure of FIG. 7A.
Figure 7A:
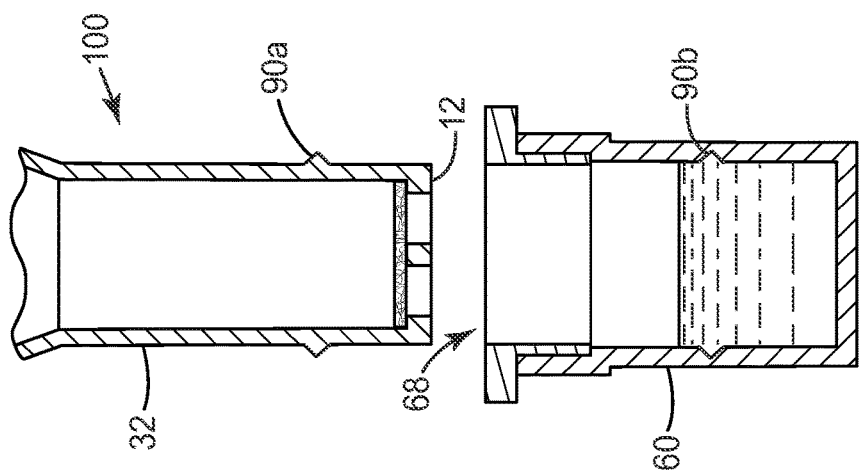
FIG. 7A is a cross-sectional side view of the outlet portion of one embodiment of the second end of a body having a first engagement structure and a corresponding closure having a second engagement structure, the first engagement structure being complementary to the second engagement structure according to the present disclosure.

FIG. 7A shows one embodiment of said complementary engagement structures. The illustrated embodiment shows the outlet 32 portion of a body 100 according to the present disclosure and a corresponding closure 60 configured to receive the outlet 32 therein. The outlet 32 comprises at least one protrusion (i.e., first engagement structure 90a) proximate the second end 30 of the body 100. In addition, the closure 60 comprises at least one complementary-shaped cavity (i.e., second engagement structure 90b) disposed in the chamber 68. Thus, when the outlet initially is received into the closure (not shown), either the first engagement structure and/or the closure reversibly deforms to permit the outlet to continue moving into the closure. When the outlet 32 moves to a predefined depth in the closure 60, the first engagement structure 90a engages the second engagement structure 90b, as shown in FIG. 7B. Although not required, the first and second engagement structures (90a and 90b, respectively) can be positioned on the body 100 and closure, respectively, so that they are engaged when the outlet fully penetrates the depth of the chamber 68, thus ensuring the movement of a portion 81 of the back-flush liquid 80 from the closure 60 into the body 100. In any embodiment, the portion 81 of back-flush liquid moved from the closure 60 into the body 100 when the outlet 32 is received into the closure 60 to a predefined depth (e.g., all the way into the closure 60) is substantially all of the back-flush liquid that was originally in the closure 60.

Figure 8:
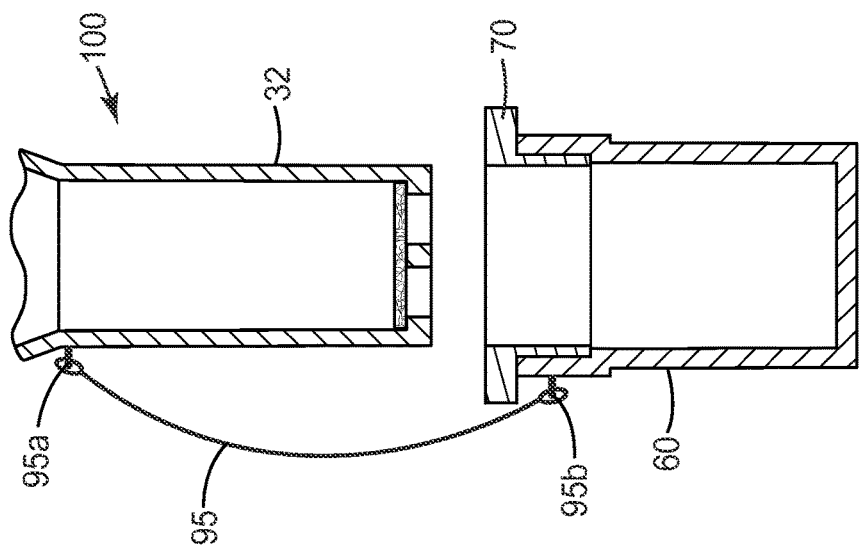
FIG. 8 is a cross-sectional side view of one embodiment of the outlet portion of the body of an assembly according to the present disclosure, wherein the assembly comprises a tether that attaches the closure to the body.

In any embodiment, the body and closure of the assembly of the present disclosure may be durably attached to each other. FIG. 8 shows one embodiment of an assembly comprising said durable attachment. The illustrated embodiment shows the outlet 32 portion of a body 100 according to the present disclosure and a corresponding closure 60, the closure 60 being attached to the body 100 via a tether 95. The tether 95 comprises a first end 95a attached to the body 100 and a second end 95b attached to the closure 60. The tether 95 can be fabricated using processes known in the art. For example, in an embodiment wherein the body and closure of the assembly are formed (e.g., injection molded) using a malleable thermoplastic material (e.g., polyethylene, polypropylene), the body 100, closure 60, and tether 95 can be molded as a unitary part. Alternatively, the parts (e.g., body 100, closure 60, and tether 95) can be formed separately (as shown in FIG. 8) and the tether 95 can be attached to the body 100 and closure 60 using any one of a variety of means known in the art such as, for example, an adhesive, a heat weld (e.g., an ultrasonic weld), a clamp, a bolt, a screw, or the like. Also shown in FIG. 8 is optional sealing element 70.

Figure 9:
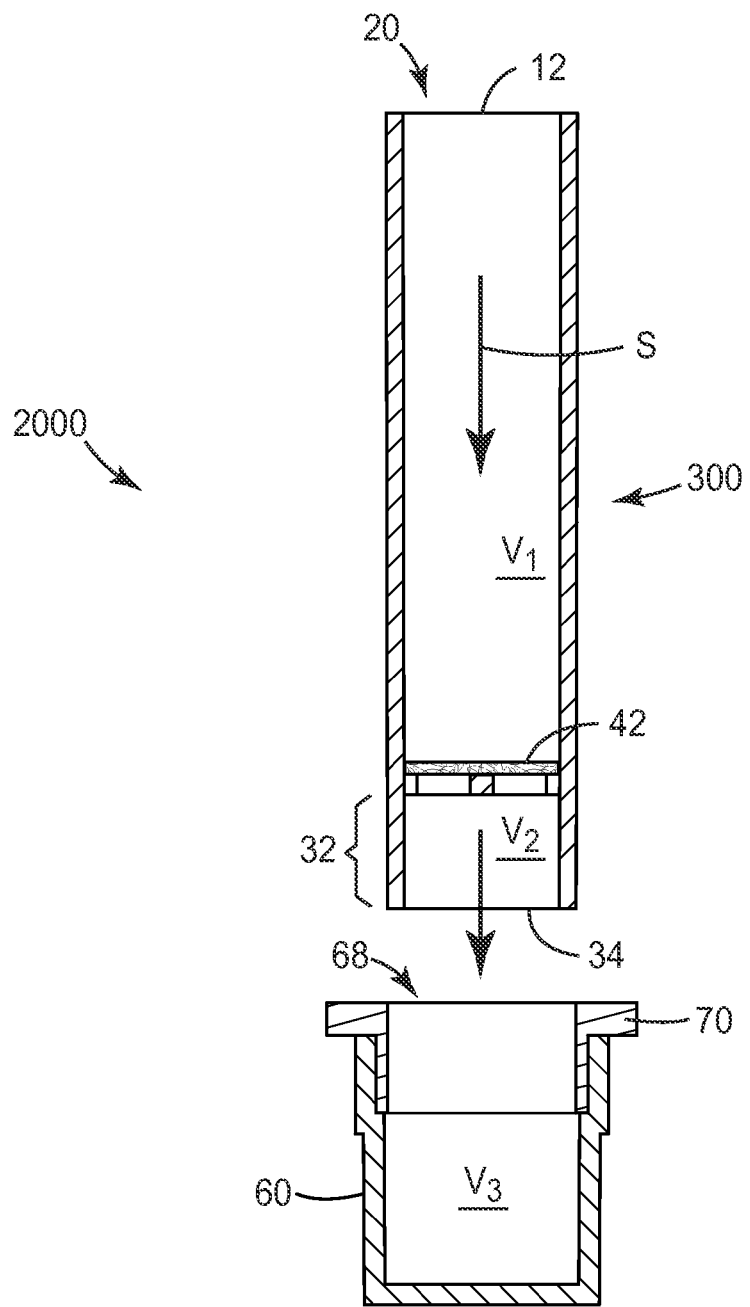
FIG. 9 is a partially-exploded side view of one embodiment of an assembly comprising a body comprising a filter element and a fluid pathway, the fluid pathway comprising two volumes that are each defined by the filter element.

In any embodiment, the filter element can be disposed in the body of the assembly at a position that is spaced apart from the second opening. FIG. 9 shows a partially-exploded cross-sectional side view of one embodiment of an assembly 2000 having a filter element 42 that is disposed in the body 300 at a position that is spaced apart from the second opening 34. A fluid pathway "S" passes through the body 300 from the first opening 12 to the second opening 34. As described above, the body 300 comprises a reservoir 20 configured to hold a fluid sample. The reservoir 20 is disposed in the fluid pathway between the first opening 12 and the filter element 42. In these embodiments, the filter element 42 defines two volumes (first volume $V_1$ and second volume $V_2$, respectively) that make up the fluid pathway. The first volume $V_1$ extends from the first opening 12 to the filter element 42 and the second volume $V_2$ extends from the second opening 34 to the filter element 42. The chamber 68 of the closure 60 defines a third volume $V_3$ that is larger than the second volume $V_2$. Thus, a back-flush liquid (not shown) can be loaded into the closure 60 and, as shown in FIGS. 6A-6C, when the outlet 32 of the body 300 is slideably urged into the closure 60, the back-flush liquid can move into the body 300 to an extent that it fills the second volume $V_2$, contacts the filter element 42 and, if desired, fills at least a portion of the first volume $V_1$.

Figure 10:
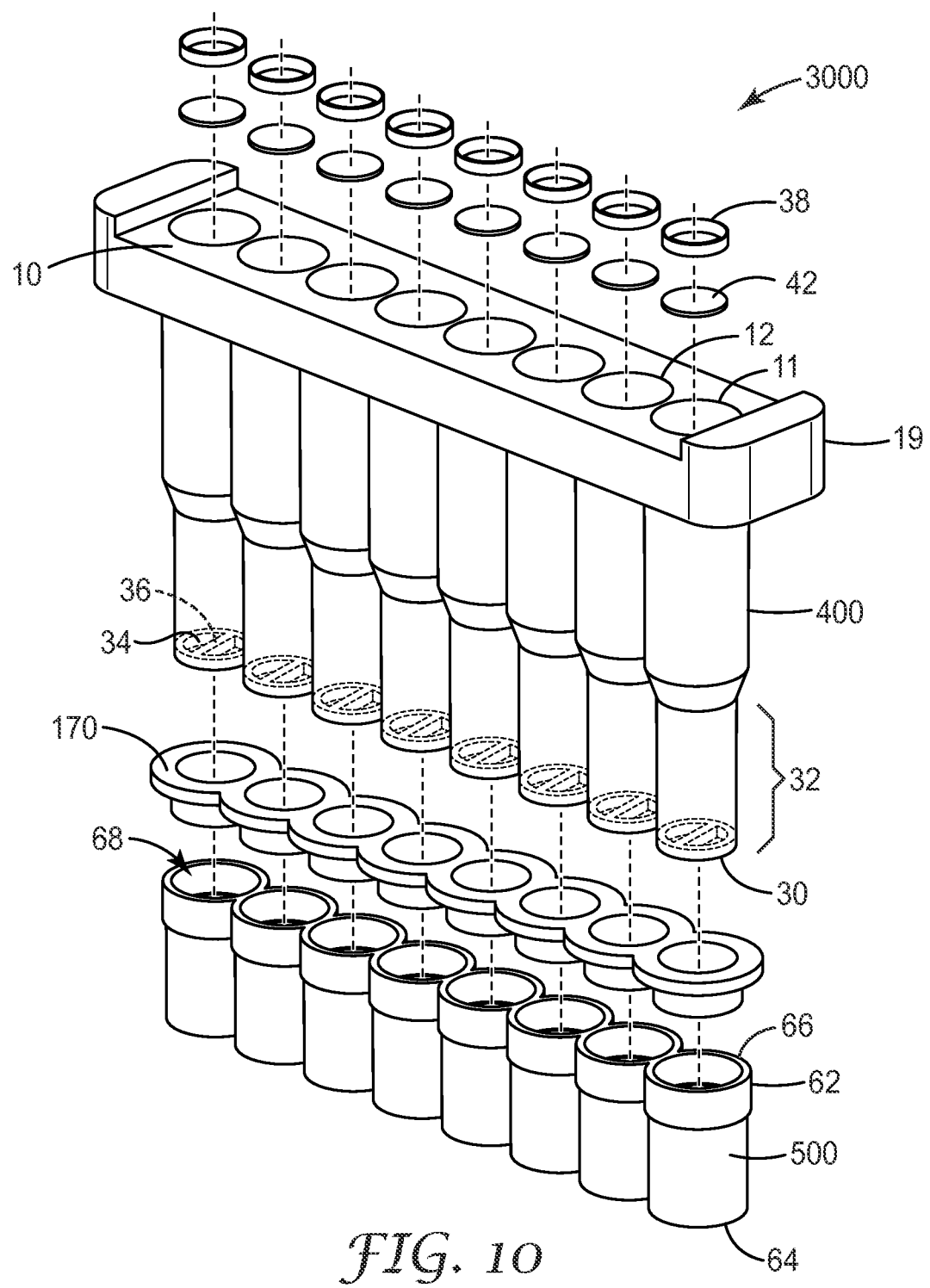
FIG. 10 is an exploded perspective view of one embodiment of an assembly comprising a first body comprising a plurality of outlets and a second body comprising a plurality of closures, wherein each of the plurality of outlets of the first body is configured to be sealingly inserted into one of the plurality of closures according to the present disclosure.

In any embodiment, an assembly of the present disclosure can be configured to process a plurality of liquid samples. Two or more of the plurality of samples can be processed simultaneously or sequentially. FIG. 10 shows an exploded view of one embodiment of an assembly 3000 for processing a plurality of liquid samples The assembly 3000 comprises a first body 400 and a second body 500. The first body 400 comprises a first end 10 with a plurality of first openings 12, a second end 30 with a plurality of second openings 34, and a plurality of hollow channels 11, each hollow channel 11 extending from one of the first openings 12 to one of the second openings 34. The first body 400 further comprises a plurality of spaced-apart outlets 32, each outlet comprising a different one of the second openings 34, and a collar 19 that can facilitate coupling the first body 400 to a source of negative pressure to assist filtration of liquid samples, as described above. The first body 400 can be made from any suitable material that is substantially impermeable to water using processes that are known in the art. Non-limiting examples of suitable materials include, for example, glass, plastic (e.g., polyethylene, polypropylene, polycarbonate), or metal. In any embodiment, the plurality of outlets 32 are configured (e.g., size, shape, spacing) so that, if desired, two or more of them can be inserted simultaneously into a standard (e.g., 96-well) heating block.

Operatively interposed in the hollow channel 11 is a filter element 42. "Operatively interposed", as used herein, means that a fluid moving through the hollow channel 11 from one end (e.g., from the first opening 12 of the first end 10) to the other end (e.g., out of the second opening 34 of the second end 30) passes through the filter element (e.g., filter element 42). Proximate the second opening 34 in each hollow channel 11 is a support piece 36, on which the filter element 42 is disposed. Optionally, the filter element 42 may be coupled to a portion of the body 400 as described above. Alternatively or additionally, in any embodiment, the filter element may be secured in a fixed position against the support piece 36 using, for example, an O-ring 38 as described above.

The second body 500 is a unitary piece comprising a plurality of spaced-apart chambers 68, each chamber having a third opening 66 that provides fluidic access to the chamber 68. The chambers 68 are shaped and dimensioned to receive (e.g., sealingly receive) one of the outlets 32 of the first body 400. In any embodiment, the assembly 3000 further may comprise a sealing member 170. The sealing member 170 is configured with a plurality of through-holes that correspond to the size, shape, and spacing of the outlets 32 and chambers 68. The sealing member 170 can be coupled to the second body 500 (e.g., by friction fit) as shown in FIG. 1 or, similarly, to the outlet (not shown). The sealing member 170 can be made from conformable materials such as, for example, silicone or rubber, which can form a seal that is substantially resistant to leakage of aqueous liquids.

During use of the assembly 3000, the chambers 68 of the second body 500 contain a back-flush liquid (not shown in FIG. 10) that is used to back-flush the filter elements 42. Thus, when the outlets 32 of the first body 400 are urged into the chambers 68 containing the back-flush liquid, the back-flush liquid is forced into the outlet 32 of each hollow channel 11 until the liquid contacts the filter element (not shown in FIG. 10, see FIGS. 6A-6C). The second body 500 can be made from any suitable material that is substantially impermeable to water using processes that are known in the art. Non-limiting examples of suitable materials include, for example, glass, plastic (e.g., polyethylene, polypropylene, polycarbonate), or metal.

In any embodiment, the first body 400 can comprise one or more positioning elements (not shown) to facilitate alignment of the first body 400 with the second body 500. A non-limiting example of one type of positioning element is described in U.S. Patent Application Publication No. US 2012/027699. The positioning element (not shown) can interact with a corresponding structure (e.g., a tab, not shown) disposed on the second body 500. A non-limiting example of one type of tab is described in U.S. Patent Application Publication No. US 2012/027699. In any embodiment, the assembly can comprise at least two positioning elements and tabs (e.g., along opposite edges of the array of hollow channels, as shown in FIG. 8 of U.S. Patent Application Publication No. US 2012/027699). Alternatively, in any embodiment, the assembly can comprise only one positioning element and tab (not shown) to facilitate the correct orientation of the first body 400 to the second body 500.

Figure 11:
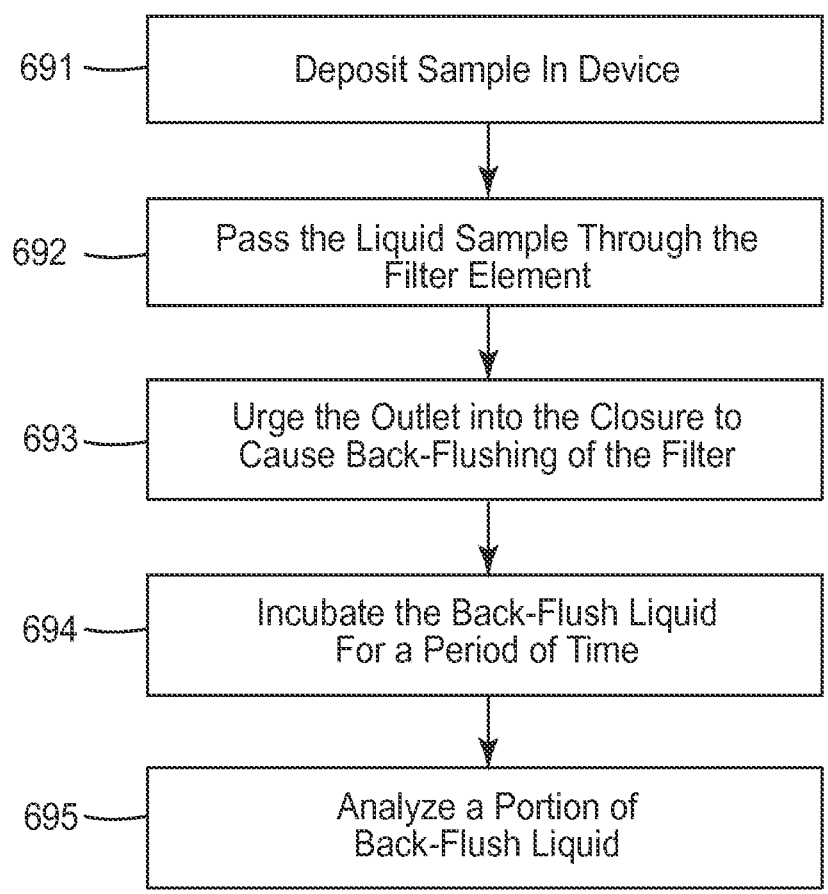
FIG. 11 is a block diagram of one embodiment of a method of detecting a microorganism in a sample according to the present disclosure.

The present disclosure also provides a method of detecting a presence or absence of a microorganism in a sample. FIG. 11 shows one embodiment of a method of detecting a presence or absence of a microorganism in a sample according to the present disclosure. The method comprises the step 691 of depositing a liquid sample suspected of containing a microorganism into a sample preparation device. The sample preparation device can be any sample preparation device described herein. In any embodiment, the sample preparation device comprises a hollow body comprising first opening, an outlet with a second opening, and a fluid pathway extending therebetween; and a filter element operatively interposed in the fluid pathway. The method further comprises the step 692 of passing the liquid sample through the filter element to retain the microorganism; the step 693 of urging the outlet into a chamber configured to sealingly receive the outlet, the chamber containing a back-flush liquid; optionally, the step 694 of incubating the back-flush liquid for a period of time; and the step 695 of analyzing a portion of the back-flush liquid to detect a presence or an absence of the microorganism. Advantageously, the entire assembly of the present disclosure can be placed in an incubator or the outlet(s) can be placed into a heating block, obviating the need to transfer the back-flush liquid to a separate container (e.g., a tube) for the heating/incubating step.

According to the method, the liquid sample can be any filterable liquid sample that may comprise a microorganism. The sample is deposited into the hollow body of the sample preparation device by pouring or pipetting, for example. In any embodiment, the liquid sample may comprise a predetermined volume of sample. Thus, after determining the presence and, optionally, the quantity of microorganisms in the predetermined volume of sample, the operator may calculate a number of microorganisms per predetermined quantity of sample (e.g., CFU/mL, CFU/g) or a threshold number of microorganisms per quantity of sample material (e.g., <1CFU/10 mL, >1CFU/10 mL).

In any embodiment, a concentration agent (e.g., a particulate material) may be added to the liquid sample whereby the microorganisms, if present in the sample, bind (e.g., reversibly bind) to the particulate material. Suitable concentration agents include those described in PCT Publication Nos. WO2009/046191 and WO2010/078404, both of which are incorporated herein by reference in their entirety. In these embodiments, the filter element can be selected with a nominal porosity suitable for retaining the concentration agent, rather than unbound microorganisms, or the filter element can be selected to retain the concentration agent and unbound microorganisms.

In any embodiment, the filter element can comprise a capture reagent (e.g., an antibody and/or an antigen-binding fragment thereof) selected to bind a specific microorganism or group of microorganisms.

In any embodiment, passing the liquid sample through the filter element can comprise actively passing the liquid through the filter element (e.g., by applying positive pressure to the first opening of the body and/or by applying negative pressure to the second opening of the body). In any embodiment, passing the liquid sample through the filter element can comprise passively passing the liquid through the filter element (e.g., by permitting gravity flow of the liquid through the filter element).

After the sample has been passed through the filter element to retain the microorganisms or a concentration element to which the microorganisms are attached, the filter element is back-flushed with a back-flush liquid in order to obtain a specimen for analysis. Back-flushing the filter element comprises contacting the filter element with a back-flush liquid. According to the present disclosure, the back-flush liquid is contacted with the filter element by urging the outlet of the sample preparation device (e.g., the body 100 or first body 400 of the present disclosure) into a chamber that holds the back-flush liquid. Urging the outlet into the chamber forms the assembly of the present disclosure. The chamber is configured to sealingly receive the outlet, thereby causing the back-flush liquid to move into the body, as shown in FIGS. 6A-6C. In any embodiment, urging the outlet into the compartment comprises urging the outlet into the compartment to an extent sufficient to cause a portion of the back-flush liquid to pass through the filter element.

After the back-flush liquid contacts the filter element, optionally, the back-flush liquid can be contacted with the filter element for a period of time. In any embodiment, the contacting the back-flush liquid with the filter element for a period of time can facilitate the permeabilization and/or lysis of microorganism cells in order to facilitate the detection an intracellular analyte (e.g., DNA, RNA). The permeabilization and/or lysis process can be enhanced when the back-flush liquid comprises a cell-lysis agent (e.g., lysozyme, a detergent). In any embodiment, contacting the back-flush liquid with the filter element for a period of time can comprise incubating the back-flush liquid in the assembly. For example, the assembly can be held at room temperature for a period of time. Alternatively, or additionally, the assembly can be placed into an incubation chamber at a temperature above ambient (e.g., at an elevated temperature of about 37° C. to about 100° C.) to facilitate the permeabilization or lysis process.

A portion of the back-flush liquid is analyzed to detect a presence or absence of a microorganism. In any embodiment, the portion can be obtained, for example, by pouring the portion out of the first opening of the assembly or by inserting a liquid-collecting device (e.g., a pipette or micropipette) through the first opening of the body to collect back-flush liquid that has passed through the filter element. Alternatively, if a permeabilizing agent or cell-lysis agent is present in the back-flush liquid, the outlet can be withdrawn from the chamber and a portion of the back-flush liquid can be removed from the closure to be analyzed. In any embodiment, the outlet can be withdrawn from the chamber and a portion of the back-flush liquid can be removed from the body (e.g., from a portion of the body located between the filter element and the first opening) to be analyzed. In any embodiment, the filter element is back-flushed with a predetermined volume of back-flush liquid. Advantageously, back-flushing the filter element with a predetermined volume of back-flush liquid permits the operator to make quantitative estimates of the number of microorganisms present per unit (e.g., volume, mass) of original sample material.

Typically, the volume of back-flush liquid that contacts and/or passes through the filter element is smaller than the liquid sample that is passed through the filter element. Accordingly, the method of the present disclosure can concentrate the microorganisms, if present in the sample, thereby increasing the detection sensitivity. In any embodiment, the method of the present disclosure can be used to concentrate the sample material retained by the filter element by at least 1.5-fold. In any embodiment, the method of the present disclosure can be used to concentrate the sample material retained by the filter element by at least 2-fold. In any embodiment, the method of the present disclosure can be used to concentrate the sample material retained by the filter element by at least 3-fold. In any embodiment, the method of the present disclosure can be used to concentrate the sample material retained by the filter element by at least 5-fold. In any embodiment, the method of the present disclosure can be used to concentrate the sample material retained by the filter element by at least 10-fold. In any embodiment, the method of the present disclosure can be used to concentrate the sample material retained by the filter element by at least 20-fold. In any embodiment, the method of the present disclosure can be used to concentrate the sample material retained by the filter element by at least 50-fold.

In any embodiment, the method further can comprise passing the liquid sample through a prefilter. In any embodiment, passing the liquid sample through a prefilter comprises passing the liquid sample through a prefilter that is disposed in the sample preparation device, as described herein. In any embodiment of the method, contacting the filter element with a back-flush liquid further can comprise contacting the prefilter element with the back-flush liquid.

Analyzing a portion of the back-flush liquid to detect a presence or an absence of the microorganism can comprise analyzing the back-flush liquid to detect an analyte that indicates the presence of a microorganism. In any embodiment, the analyte may indicate the presence of a particular microorganism (e.g., a particular species of microorganism, a particular genus of microorganisms, a particular group (e.g., toxin-producing) microorganism, or the like). In any embodiment, detecting the analyte comprises culturing a microorganism or detecting a biomolecule. In any embodiment, detecting a biomolecule comprises detecting a polynucleotide, a polypeptide, or a polysaccharide.

The biomolecules can be detected by any method known in the art including, for example, nucleic acid hybridization and/or amplification techniques (e.g., PCR, rtPCR, LCR, and the like) or immunodetection techniques (e.g., ELISA, immunoblotting, immunochromatography). In a particularly preferred embodiment, detecting a biomolecule comprises detecting a nucleic acid analyte using the LAMP-BART isothermal nucleic acid detection technology of the 3M Molecular Diagnostic System sold by 3M Company (St. Paul, Minn.). This technology is described, for example, in U.S. Pat. Nos. 7,371,545; 7,374,913; 7,494,790; and 8,309,308; and US Patent Application Publication No. US 2012/0157326; all of which are incorporated herein by reference in their entirety.

It is contemplated that, in any embodiment, analyzing a portion of the back-flush liquid to detect a presence of a microorganism further can comprise analyzing the portion to determine a quantity of microorganisms present in the portion. Thus, it is also contemplated that the operator can calculate the number of microorganisms, if present, in the sample and use the information to estimate the number of microorganisms present in the original liquid sample.

In yet another aspect, the present disclosure provides a kit. The kit may comprise the components of any embodiment of the assembly disclosed herein. For example, in any embodiment, the kit can comprise a hollow body comprising first opening, an outlet with a second opening, and a fluid pathway extending therebetween; a filter element as described herein operatively interposed in the fluid pathway; and a closure as described herein comprising a third opening and a chamber, wherein the chamber and the outlet are configured so that the outlet is sealingly received in the compartment. In any embodiment, the kit further can comprise a prefilter, a wash solution, a reagent to facilitate the release of the analyte from a filter element, a cell lysis reagent, a detection reagent, a device for culturing and enumerating microorganisms, or a combination of any two or more of the foregoing accessories.

EMBODIMENTS

Embodiment A is an assembly, comprising:

a hollow body comprising first opening, an outlet with a second opening, and a fluid pathway extending therebetween;

a filter element operatively interposed in the fluid pathway; and a closure comprising a third opening and a chamber, the closure being slideably engaged with the outlet;

wherein the chamber and the outlet are dimensioned so that the outlet is sealingly engaged with the chamber.

Embodiment B is the assembly of Embodiment A, wherein the hollow body further comprises a reservoir dimensioned to receive a predefined volume of liquid sample, wherein the fluid pathway comprises the reservoir.

Embodiment C is the assembly of Embodiment A or Embodiment B wherein, when the closure is coupled to the outlet, the closure is sealingly coupled to the outlet.

Embodiment D is the assembly of any one of the preceding Embodiments, further comprising a tether comprising a tether first end and a tether second end, wherein the tether first end is coupled to the closure.

Embodiment E is the assembly of Embodiment D, wherein the tether second end is coupled to the body.

Embodiment F is an assembly, comprising:

a first body comprising a plurality of hollow channels, each hollow channel extending from a first opening to a second opening, each second opening being disposed in one of a plurality of outlets;

a plurality of filter elements, wherein each of the filter elements is operatively interposed in one of the plurality of hollow channels; and a plurality of closures, each closure comprising a third opening and a chamber, each of the plurality of closures being slideably engaged with a different outlet of the plurality of outlets;

wherein each of the plurality of closures and each of the plurality of outlets are dimensioned so that one of the plurality of outlets is sealingly engaged with a corresponding chamber of the plurality of chambers.

Embodiment G is the assembly of Embodiment F, wherein the plurality of closures are formed in a unitary second body, wherein the chambers are configured so that two or more outlets simultaneously can be slideably engaged with two or more of the plurality of closures in the unitary body.

Embodiment H is the assembly of Embodiment F or Embodiment G, wherein each hollow channel comprises a reservoir, the reservoir being dimensioned to receive a predefined volume of liquid sample.

Embodiment I is the assembly of any one of Embodiments F through H wherein, when each of the plurality of closures is coupled to one of the plurality of outlets, each closure is sealingly coupled to the one of the plurality of outlets.

Embodiment J is the assembly of any one of the preceding Embodiments, wherein the body further comprises a first engagement structure, wherein the closure further comprises a second engagement structure complementary to the first engagement structure.

Embodiment K is the assembly of any one of Embodiments F through J, further comprising a plurality of tethers, each tether comprising a tether first end and a tether second end, wherein each tether first end is coupled to one of the plurality of closures, wherein each of the plurality of closures has a tether coupled thereto.

Embodiment L is the assembly of Embodiment K, wherein each of the plurality of tether second ends is coupled to the body.

Embodiment M is the assembly of any one of the preceding Embodiments, further comprising a reagent disposed in at least one of the pathways or at least one of the closures.

Embodiment N is the assembly of Embodiment M, wherein the reagent comprises a reagent to facilitate the release of an analyte from the filter element.

Embodiment O is the assembly of Embodiment M or Embodiment N, wherein the reagent comprises a liquid reagent.

Embodiment P is the assembly of any one of the preceding Embodiments:

wherein the assembly comprises a first fluid pathway extending to a first second opening at a first outlet, a first filter element operatively interposed in the first fluid pathway, and a first closure having a chamber dimensioned to sealingly receive the first outlet; wherein the first fluid pathway comprises two volumes defined by the filter element;

a first volume extending from the filter element to the first opening; and a second volume extending from the disposed between the filter element and the second opening;

wherein the chamber of the first closure defines a third volume that is greater than the second volume.

Embodiment Q is a method, comprising:

depositing a liquid sample suspected of containing a microorganism into a sample preparation device, the sample preparation device comprising:

a hollow body comprising first opening, an outlet with a second opening, and a fluid pathway extending therebetween;

a filter element operatively interposed in the fluid pathway;

passing the liquid sample through the filter element to retain the microorganism;

urging the outlet into a chamber configured to sealingly receive the outlet, the chamber containing a back-flush liquid;

wherein urging the outlet into the chamber comprises urging the outlet into the chamber to an extent sufficient to cause the back-flush liquid to contact the filter element; and analyzing a portion of the back-flush liquid to detect a presence or an absence of the microorganism.

Embodiment R is the method of Embodiment Q, wherein urging the outlet into the chamber comprises urging the outlet into the chamber to an extent sufficient to cause a portion of the back-flush liquid to pass through the filter element.

Embodiment S is the method of Embodiment R, wherein analyzing a portion of the back-flush liquid to detect a presence or an absence of the microorganism comprises analyzing a quantity of the portion of the back-flush liquid.

Embodiment T is the method of any one of Embodiments Q through S, further comprising passing the liquid sample through a prefilter.

Embodiment U is the method of Embodiment T, wherein passing the liquid sample through a prefilter comprises passing the liquid sample through a prefilter that is disposed in the sample preparation device.

Embodiment V is the method of embodiment U, wherein contacting the filter element with a back-flush liquid further comprises contacting the prefilter element with the back-flush liquid.

Embodiment W is the method of any one of Embodiments Q through V, further comprising passing a wash solution through the filter element.

Embodiment X is the method of any one of Embodiments Q through W, further comprising contacting the filter element with a reagent to facilitate permeabilization of a microorganism.

Embodiment Y is the method of Embodiment X, wherein the reagent to facilitate the permeabilization of a microorganism comprises a cell lysis reagent.

Embodiment Z is the method of Embodiment X or Embodiment Y, wherein the back-flush liquid comprises the reagent to facilitate permeabilization of a microorganism.

Embodiment AA is the method of any one of Embodiments Q through Z, further comprising:

after urging the outlet into the chamber and before analyzing the portion of the back-flush liquid, removing the outlet from the chamber.

Embodiment BB is the method of any one of Embodiments Q through AA, further comprising contacting the back-flush liquid with the filter element for a period of time.

Embodiment CC is the method of Embodiment BB, wherein contacting the back-flush liquid with the filter element for a period of time comprises contacting the back-flush liquid with the filter element at a temperature above ambient.

Embodiment DD is the method of any one of Embodiments Q through CC, wherein detecting the analyte comprises culturing a microorganism or detecting a biomolecule.

Embodiment EE is the method of Embodiment DD, wherein detecting a biomolecule comprises detecting a polynucleotide, a polypeptide, or a polysaccharide.

Embodiment FF is a kit, comprising:

a hollow body comprising first opening, an outlet with a second opening, and a fluid pathway extending therebetween;

a filter element coupled to the body such that the filter is operatively interposed in the fluid pathway; and a closure comprising a third opening and a chamber, wherein the chamber and the outlet are configured so that the second end can be sealingly received in the chamber.

Embodiment GG is the kit of Embodiment FF, further comprising a prefilter, a wash solution, a reagent to facilitate the release of the analyte from a filter element, a cell lysis reagent, a detection reagent, or a device for culturing and enumerating microorganisms.

Various modifications may be made without departing from the spirit and scope of the invention. These and other embodiments are within the scope of the following claims.

Advantages and embodiments of this disclosure are further illustrated by the following examples, but the particular materials and amounts thereof recited in these examples, as well as other conditions and details, should not be construed to unduly limit this disclosure. All materials are commercially available or known to those skilled in the art unless otherwise stated or apparent.

EXAMPLES

Buffer Reagent

The buffer reagent was prepared as a solution of the components listed in Table 1 in one liter of deionized water. All of the components listed in Table 1 were obtained from the Sigma-Aldrich Company, St. Louis, Mo. The buffer reagent also served as the DNA lysis reagent.

TABLE 1

| Component | CAS Number | Amount (grams) |
| --- | --- | --- |
| potassium chloride | 7447-40-7 | 3.19 |
| ammonium sulfate | 7783-20-2 | 1.41 |
| TRIS hydrochloride | 1185-53-1 | 2.72 |
| Proclin ™ 950 Preservative (9.5% of 2-methyl-4-isothiazolin-3-one as the active ingredient) | 2682-20-4 | 0.53 |
| Triton ™ X-100 | 9002-93-1 | 1.10 |
| polyvinylpyrrolidone (PVP) | 9003-39-8 | 4.30 |

Sample Preparation Assembly Body

Body portions of the assemblies were prepared using the syringe barrel housings from 3M Empore™ C8-SD 3 mL Extraction Cartridges (identified by UPC number 00051115087820 or part number 98060401928 and commercially available from the 3M Company, St. Paul, Minn.). The housings were molded from polypropylene and contained a barrel shaped reservoir section (about 60 mm in length with a reservoir capacity of about 3 mL) and a slip tip section (about 13 mm in length with an inner diameter opening of about 2 mm) The pre-filter and membrane components of the cartridge were discarded, while the sealing rings were saved and reused.

Two different types of filter discs were prepared. The first circular filter disc (10 mm diameter) was die cut from a Versapor® acrylic copolymer membrane disc filter having a pore size of 0.8 microns and a nominal thickness of 94 microns (part number 66404, Pall Corporation, Port Washington, N.Y.). The second circular filter disc (10 mm diameter) was die cut from a Versapor® acrylic copolymer membrane disc filter having a pore size of 5 microns and a nominal thickness of 94 microns (part number 66017, Pall Corporation). The body portion was constructed by mounting a filter stack containing a 0.8 micron filter disc combined with a 5 micron filter disc into the bottom of the syringe barrel. The filter stack was prepared so that one face of each filter disc was in contact with a face of the other disc. The filter stack was mounted in the syringe barrel so that the exposed face of the 0.8 micron filter was oriented toward the slip tip end of the syringe barrel housing. The two exposed faces of the filter stack were each in contact with a sealing ring. The two sealing rings secured the filter stack inside the barrel.

In order to reduce non-specific macromolecule binding to the interior surfaces of the body portion, the interior was rinsed with 100 microliters of a 0.3% by weight aqueous solution of Novec™ FC4430 Fluorosurfactant (3M Company), and the surfactant was drawn through the filter stack component using vacuum (500 torr).

Spiked Food Sample Preparation

A food sample of salmon and cream cheese was prepared by adding a 25 g of the salmon and cream cheese product to a plastic enrichment bag containing 225 mL of Modified Listeria Recovery Broth (product number MLRB500, 3M Company). The enrichment bag was sealed and processed for two minutes in a Seward Stomacher® Model #400 Circulator (Seward Laboratory Systems Inc., Port Saint Lucie, Fla.). The enrichment bag was then incubated at 37° C. for 28 hours. The enrichment bag was cooled to ambient temperature.

A Listeria monocytogenes (ATCC-19118) sample was obtained from a frozen stock reference standard that was subcultured and then serially diluted with Modified Listeria Recovery Broth (product number MLRB500, 3M Company) to a concentration of $1 \times 10^5$ cfu/mL. The concentration was confirmed using a 3M Petrifilm™ Aerobic Count Plate (catalog number 6400, 3M Company). The enrichment bag was opened and spiked with 250 microliters of the *Listeria* sample. The bag was closed and then kneaded by hand for 30 seconds.

A filter bag for clarifying the spiked sample was prepared using the filter medium from a 3M 744B filter cartridge (3M Company). The filter medium was a polypropylene melt-blown microfiber with a reported particle removal efficiency of 99% for 5 micron particles. The filter medium was carefully removed from the cartridge assembly and cut into 1 inch by 2 inch fragments. The fragments were treated with a 2 wt/wt % solution of Tween® 20 (Sigma-Aldrich Company) in methanol by immersing each fragment in a bath of Tween® 20 solution for five minutes. The fragments were then air dried overnight. A filter bag was assembled by overlaying one of the fragments with another fragment and heat sealing the juxtaposed fragments together on three sides. The filter bag was placed in the enrichment bag and oriented so that the opening in the filter bag was maintained above the fluid level in the enrichment bag. Approximately 1 mL of enrichment liquid flowed by gravity through the filter medium into the filter bag. A pipette was subsequently used to withdraw the clarified enrichment sample from the filter bag for further processing.

Example 1

The body portion of a sample preparation assembly (described above) was attached to a vacuum manifold. A *Salmonella enterica* sample (ATCC 14028) was obtained from a frozen stock reference standard that was subcultured and then serially diluted with buffered peptone water broth (BPW-ISO, 3M Company) to a concentration of $1 \times 10^2$ cfu/mL. The concentration was confirmed using a 3M Petrifilm™ Aerobic Count Plate (catalog number 6400, 3M Company). An aliquot of the *Salmonella* culture sample (0.5 mL) was added by pipette to the reservoir section of the assembly (added through the opening in the assembly opposite from the tip end) and the liquid was drawn by vacuum (about 500 torr) through the filter component and then through the tip of the apparatus into a collection vessel. Next, 0.5 mL of the buffer reagent (described above) was added by pipette to the reservoir section of the assembly (added through the opening in the assembly opposite from the tip end) and the liquid was drawn by vacuum (about 500 torr) through the filter component and then through the tip of the apparatus into the collection vessel.

A 2 mL glass vial (product number 5182-0543 commercially available from Agilent Technologies, Santa Clara, Calif.) was used as the closure for the sample preparation assemblies. The vials were filled with the buffer reagent and fitted with a Snap-It cap (product number C4011-54 commercially available from the National Scientific Company, Rockwood, Tenn.) to seal them. The polypropylene cap contained a PTFE/silicone septum. The reagent filled vial with cap served as the closure element for the finished filter assembly. The slip tip of the filter assembly body portion was inserted into the vial through the septum. Insertion of the tip into the vial caused approximately 175 microliters of the buffer reagent to be back-flushed through the filter into the reservoir of the body portion.

The vial and the body portion were disengaged and the opening in the slip tip of the assembly body was closed by heat sealing. The body portion of the assembly was then heated at 100° C. for five minutes in an aluminum dry block heater (part number 13259-052) fitted with an insert block for heating tubes (part number 13259-242). Both the block heater and insert were obtained from VWR Scientific, Radnor, Pa. The assembly body was removed from the heating block and cooled to ambient temperature.

Isothermal DNA amplification and bioluminescence detection of the pathogen sample was conducted using a 3M Molecular Detection System Instrument with the associated *Salmonella* detection assay kit (3M Company). A 20 microliter aliquot was removed from the reservoir of the assembly body using a pipette and transferred to an assay tube provided in the assay kit. The aliquot and reagent pellet in the assay tube were mixed by sequentially drawing the liquid into the pipette and then discharging it back into the assay tube according to the kit instructions. The assay tube was placed in the instrument and the automated assay was started. The pathogen detection was complete in about 75 minutes. A total of four replicates were tested and the instrument detected the *Salmonella* pathogen in all four of the replicates (Table 2).

Comparative Example 1

The general procedure of Example 1 was followed with the exception that the back-flush procedure was not used to add the buffer reagent. The body portion of the assembly was attached to a vacuum manifold. The *Salmonella* culture sample (0.5 mL of an approximately $1 \times 10^2$ cfu/mL concentration) was added by pipette to the reservoir section of the assembly (added through the opening in the assembly opposite from the tip end) and the liquid was drawn by vacuum (about 500 torr) through the filter component and then through the tip of the apparatus into a collection vessel. Next, 0.5 mL of the buffer reagent was added by pipette to the reservoir section of the assembly (added through the opening in the assembly opposite from the tip end) and the liquid was drawn by vacuum through the filter component and then through the tip of the apparatus into the collection vessel.

The assembly body was removed from the vacuum manifold and the opening in the slip tip of the body was closed by heating sealing. The buffer reagent (175 microliters) was added by pipette to the reservoir section of the body (added through the opening in the assembly opposite from the tip end). The buffer reagent was mixed by sequentially drawing the liquid into the pipette and then discharging it back into the body. The assembly was then heated at 100° C. for five minutes using the dry block heater system described in Example 1. The body was removed from the heating block and cooled to ambient temperature.

Isothermal DNA amplification and bioluminescence detection of the pathogen sample was conducted using a 3M Molecular Detection System Instrument with the associated *Salmonella* assay kit (3M Company). A 20 microliter aliquot was removed from the reservoir of the assembly body using a pipette and transferred to an assay tube provided in the assay kit. The aliquot and reagent pellet in the assay tube were mixed by sequentially drawing the liquid into the pipette and then discharging it back into the assay tube according to the kit instructions. The assay tube was placed in the instrument and the automated assay was started. The pathogen detection was complete in about 75 minutes. A total of four replicates were tested and the instrument detected the *Salmonella* pathogen in only two of the four of the replicates (Table 2).

Reference Examples 1-7

Seven reference examples were prepared from a frozen stock reference standard of *Salmonella enterica* (ATCC 14028) that was subcultured and then serially diluted with buffered peptone water broth (BPW-ISO, 3M Company). The concentrations of the seven reference examples ranged from $1.5 \times 10^2$ cfu/mL to $1.0 \times 10^5$ cfu/mL (Table 2). For each reference example, a 20 microliter aliquot was added to a glass vial containing 0.58 mL of the buffer reagent and the vial was heated at 100° C. for five minutes using the dry block heater described in Example 1. The vial was removed from the heating block and cooled to ambient temperature. Isothermal DNA amplification and bioluminescence detection of the pathogen sample was conducted using a 3M Molecular Detection System Instrument with the associated *Salmonella* detection assay kit (3M Company). A 20 microliter aliquot was removed from the vial using a pipette and transferred to an assay tube provided in the assay kit. The aliquot and reagent pellet in the assay tube were mixed by sequentially drawing the liquid into the pipette and then discharging it back into the assay tube according to the kit instructions. The assay tube was placed in the instrument and the automated assay was started. The pathogen detection was complete in about 75 minutes. A total of four replicates were tested for each reference example (Table 2). For the reference examples with pathogen concentration at $1.5 \times 10^2$, $6.0 \times 10^2$, and $1.3 \times 10^3$ cfu/mL, the instrument did not detect the *Salmonella* pathogen in any of the replicates. For the reference example with pathogen concentration at $2.5 \times 10^3$ cfu/mL, the instrument detected the *Salmonella* pathogen in only one of four replicates. For the reference examples with pathogen concentrations at $5.0 \times 10^3$ cfu/mL and $1.0 \times 10^4$ cfu/mL, the instrument detected the *Salmonella* pathogen in three of four replicates. For the reference example with pathogen concentration at $1.0 \times 10^5$ cfu/mL, the instrument detected the *Salmonella* pathogen in all four replicates.

TABLE 2

*Salmonella* Pathogen

| | Initial Concentration of the *Salmonella* Sample (cfu/mL) | Number of Replicates with *Salmonella* Detected | Number of Replicates with *Salmonella* Not Detected |
|---|---|---|---|
| Example 1 | $1.0 \times 10^2$ | 4 | 0 |
| Comparative Example 1 | $1.0 \times 10^2$ | 2 | 2 |
| Reference Example 1 | $1.5 \times 10^2$ | 0 | 4 |
| Reference Example 2 | $6.0 \times 10^2$ | 0 | 4 |
| Reference Example 3 | $1.3 \times 10^3$ | 0 | 4 |
| Reference Example 4 | $2.5 \times 10^3$ | 1 | 3 |
| Reference Example 5 | $5.0 \times 10^3$ | 3 | 1 |
| Reference Example 6 | $1.0 \times 10^4$ | 3 | 1 |
| Reference Example 7 | $1.0 \times 10^5$ | 4 | 0 |

Example 2

The body portion of the sample preparation assembly (described above) was attached to a vacuum manifold and 0.5 mL of the clarified filtrate from the spiked food sample (described above) was added by pipette to the reservoir section of the assembly (added through the opening in the assembly opposite from the tip end) and the liquid was drawn by vacuum (about 500 torr) through the filter component and then through the tip of the apparatus into a collection vessel. Next, 0.5 mL of the buffer reagent was added by pipette to the reservoir section of the assembly (added through the opening in the assembly opposite from the tip end) and the liquid was drawn by vacuum (about 500 torr) through the filter component and then through the tip of the apparatus into the collection vessel.

A 2 mL glass vial described in Example 1 was filled with the buffer reagent and fitted with the Snap-It cap closure described in Example 1. The slip tip of the body portion was inserted into the vial through the septum. Insertion of the tip into the vial caused approximately 175 microliters of the buffer reagent to be back-flushed through the filter into the reservoir of the body portion.

The vial and the body portion were disengaged and the opening in the slip tip of the assembly body was closed by heat sealing. The body portion of the assembly was then heated at 100° C. for five minutes using the dry block heater system described in Example 1. The assembly body was removed from the heating block and cooled to ambient temperature.

Isothermal DNA amplification and bioluminescence detection of the pathogen sample was conducted using a 3M Molecular Detection System Instrument with the associated *Listeria* detection assay kit (3M Company). A 20 microliter aliquot was removed from the reservoir of the assembly body using a pipette and transferred to an assay tube provided in the assay kit. The aliquot and reagent pellet in the assay tube were mixed by sequentially drawing the liquid into the pipette and then discharging it back into the assay tube according to the kit instructions. The assay tube was placed in the instrument and the automated assay was started. The pathogen detection was complete in about 75 minutes. A total of three replicates were tested and the instrument detected the *Listeria* pathogen in two of the three replicates (Table 3).

Comparative Example 2

A 20 microliter aliquot from the clarified filtrate of the spiked food sample (described above) was added to a glass vial containing 0.58 mL of the buffer reagent and the vial was heated at 100° C. for fifteen minutes using the dry block heater described in Example 1. The vial was removed from the heating block and cooled to ambient temperature. Isothermal DNA amplification and bioluminescence detection of the pathogen sample was conducted using a 3M Molecular Detection System Instrument with the associated *Listeria* detection assay kit (3M Company). A 20 microliter aliquot was removed from the vial using a pipette and transferred to an assay tube provided in the assay kit. The aliquot and reagent pellet in the assay tube were mixed by sequentially drawing the liquid into the pipette and then discharging it back into the assay tube according to the kit instructions. The assay tube was placed in the instrument and the automated assay was started. The pathogen detection was complete in about 75 minutes. A total of nine replicates were tested and the instrument did not detect the *Listeria* pathogen in any of the replicates (Table 3).

TABLE 3

Food Sample Spiked with *Listeria* Pathogen

| | Number of Replicates with *Listeria* Detected | Number of Replicates with *Listeria* Not Detected |
|---|---|---|
| Example 2 | 2 | 1 |
| Comparative Example 2 | 0 | 9 |

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

Various modifications may be made without departing from the spirit and scope of the invention. These and other embodiments are within the scope of the following claims.

What is claimed is:

1. A method, comprising:
   depositing a liquid sample suspected of containing a microorganism into a first opening of a hollow body of a sample-preparation device, the sample-preparation device comprising:
      the hollow body, which comprises the first opening, an outlet with a second opening, and a fluid pathway extending between the first opening and the second opening; and
      a filter element operatively interposed in the fluid pathway;
   passing the liquid sample through the filter element to retain the microorganism;
   urging the outlet into a chamber configured to sealingly receive the outlet, the chamber containing a back-flush liquid;
      wherein urging the outlet into the chamber comprises urging the outlet into the chamber to an extent sufficient to cause the back-flush liquid to pass from the chamber through the filter element and into the outlet; and
   removing a portion of the back-flush liquid from the outlet and analyzing the portion to detect a presence or an absence of the microorganism.

2. The method of claim 1, further comprising passing the liquid sample through a prefilter.

3. The method of claim 2, wherein the passing the liquid sample through a prefilter comprises passing the liquid sample through a prefilter that is disposed in the sample-preparation device.

4. The method of claim 1, further comprising contacting the filter element with a reagent to facilitate permeabilization of the microorganism.

5. The method of claim 4, wherein the reagent to facilitate permeabilization of the microorganism comprises a cell lysis reagent.

6. The method of claim 1, further comprising:
   after urging the outlet into the chamber and before analyzing the portion of the back-flush liquid, removing the outlet from the chamber.

7. The method of claim 1, further comprising contacting the back-flush liquid with the filter element for a period of time.

8. The method of claim 4, wherein the back-flush liquid comprises the reagent to facilitate permeabilization of the microorganism.

9. The method of claim 1, wherein analyzing the portion comprises detecting an analyte, wherein detecting the analyte comprises culturing the microorganism or detecting a biomolecule.

10. The method of claim 9, wherein detecting the biomolecule comprises detecting a polynucleotide, a polypeptide, or a polysaccharide.

* * * * *

UNITED STATES PATENT AND TRADEMARK OFFICE
CERTIFICATE OF CORRECTION

| | | |
|---|---|---|
| PATENT NO. | : 9,677,981 B2 | Page 1 of 1 |
| APPLICATION NO. | : 14/774149 | |
| DATED | : June 13, 2017 | |
| INVENTOR(S) | : Gregory W. Sitton et al. | |

It is certified that error appears in the above-identified patent and that said Letters Patent is hereby corrected as shown below:

In the Specification

Column 1,
Line 66, "outlets;" should read --outlets.--.

Column 5,
Line 53, "*anthracia,*" should read --*anthracis,*--.
Line 57, "*parahemolyticus,*" should read --*parahaemolyticus*--.
Line 58, "*cholerasuis,*" should read --*choleraesuis,*--.

Column 6,
Line 38, ""5")" should read --"S")--.

Column 10,
Line 47, "samples" should read --samples.--.

Column 18,
Line 23, "2 mm)" should read --2 mm).--.

Signed and Sealed this
Twenty-fourth Day of April, 2018

Andrei Iancu
*Director of the United States Patent and Trademark Office*